United States Patent
Sommerich

(10) Patent No.: US 8,039,591 B2
(45) Date of Patent: Oct. 18, 2011

(54) FLOWABLE COLLAGEN MATERIAL FOR DURAL CLOSURE

(75) Inventor: Robert E. Sommerich, Norton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 16 days.

(21) Appl. No.: 12/427,380

(22) Filed: Apr. 21, 2009

(65) Prior Publication Data

US 2009/0269413 A1    Oct. 29, 2009

Related U.S. Application Data

(60) Provisional application No. 61/047,149, filed on Apr. 23, 2008.

(51) Int. Cl.
*A61K 38/17* (2006.01)
(52) U.S. Cl. .......................... 530/356; 514/12
(58) Field of Classification Search .................. None
See application file for complete search history.

(56) References Cited

U.S. PATENT DOCUMENTS

| | | | |
|---|---|---|---|
| 2,465,357 A | 3/1949 | Correll |
| 2,492,458 A | 12/1949 | Bering |
| 3,157,524 A | 11/1964 | Artandi |
| 3,364,200 A | 1/1968 | Aston et al. |
| 3,366,440 A | 1/1968 | Nuwayser |
| 3,520,402 A | 7/1970 | Nichols |
| 3,526,228 A | 9/1970 | Lyng |
| 3,632,361 A | 1/1972 | Battista |
| 3,742,955 A | 7/1973 | Battista et al. |
| 3,800,792 A | 4/1974 | McKnight et al. |
| 3,939,831 A | 2/1976 | Cioca et al. |
| 4,006,220 A | 2/1977 | Gottlieb |
| 4,016,877 A | 4/1977 | Cruz, Jr. et al. |
| 4,066,083 A | 1/1978 | Ries et al. |
| 4,089,333 A | 5/1978 | Utsuo et al. |
| 4,140,537 A | 2/1979 | Luck et al. |
| 4,148,664 A | 4/1979 | Cruz, Jr. |
| 4,185,011 A | 1/1980 | Eckmayer et al. |
| 4,215,200 A | 7/1980 | Miyata et al. |
| 4,233,360 A | 11/1980 | Luck et al. |
| 4,238,480 A | 12/1980 | Sawyer |
| 4,271,070 A | 6/1981 | Miyata et al. |
| 4,280,954 A | 7/1981 | Yannas et al. |
| 4,294,241 A | 10/1981 | Miyata et al. |
| 4,376,071 A | 3/1983 | Jennings et al. |
| 4,404,033 A | 9/1983 | Steffan et al. |
| 4,404,970 A | 9/1983 | Sawyer |
| 4,407,787 A | 10/1983 | Stemberger et al. |
| 4,412,947 A | 11/1983 | Cioca |
| 4,522,753 A | 6/1985 | Yannas et al. |
| 4,578,067 A | 3/1986 | Cruz, Jr. |
| 4,597,762 A | 7/1986 | Walter et al. |
| 4,600,533 A | 7/1986 | Chu |
| 4,606,910 A | 8/1986 | Sawyer |
| 4,655,980 A | 4/1987 | Chu |
| 4,689,399 A | 8/1987 | Chu |
| 4,725,671 A | 2/1988 | Chu et al. |
| 4,738,849 A | 4/1988 | Sawyer |
| 4,787,900 A | 11/1988 | Yannas |
| 4,798,800 A | 1/1989 | Timpl et al. |
| 4,837,285 A | 6/1989 | Berg et al. |
| 4,931,546 A | 6/1990 | Tardy et al. |
| 4,947,840 A | 8/1990 | Yannas et al. |
| 4,948,540 A | 8/1990 | Nigam |
| 4,950,483 A | 8/1990 | Ksander et al. |
| 4,963,146 A | 10/1990 | Li |
| 4,970,298 A | 11/1990 | Silver et al. |
| 5,019,087 A | 5/1991 | Nichols |
| 5,028,695 A | 7/1991 | Eckmayer et al. |
| 5,071,878 A | 12/1991 | Herschler |
| 5,110,604 A | 5/1992 | Chu et al. |
| 5,171,574 A | 12/1992 | Kuberasampath et al. |
| 5,201,745 A | 4/1993 | Tayot et al. |
| 5,206,028 A | 4/1993 | Li |
| 5,209,776 A | 5/1993 | Bass et al. |
| 5,215,904 A | 6/1993 | Gould et al. |
| 5,227,301 A | 7/1993 | Turner et al. |
| 5,412,076 A | 5/1995 | Gagnieu et al. |

(Continued)

FOREIGN PATENT DOCUMENTS

CA    2140834 A1    7/1995

(Continued)

OTHER PUBLICATIONS

Liu et al. "A collagen-based sealant to prevent in vivo reformation of epidural scar adhesions in an adult rat laminectomy model", J. Neurosurg (Spine 1), 2002, vol. 97, pp. 69-74.*

(Continued)

*Primary Examiner* — Suzanne M Noakes

(74) *Attorney, Agent, or Firm* — Nutter McClennen & Fish LLP

(57) ABSTRACT

Flowable graft materials are provided which comprise collagen powder and a liquid in an amount sufficient to impart a flowable consistency to the material. The graft materials are sufficiently formable and pliable so as to provide both superior contact with and easier access to a surgical site than typical, more rigid grafts such as collagen sheets. These flowable materials may also be in a fluidized, paste-like and/or gel-like state and may be moldable and/or ejectable. The flowable collagen materials reduce and/or eliminate post implantation problems associated with other materials, e.g. synthetic dural sealants (hemostasis products), such as product swelling after application and implantation. The flowable graft materials are particularly useful as a dural graft.

5 Claims, No Drawings

U.S. PATENT DOCUMENTS

| | | | |
|---|---|---|---|
| 5,418,222 | A | 5/1995 | Song et al. |
| 5,512,301 | A | 4/1996 | Song et al. |
| 5,531,791 | A | 7/1996 | Wolfinbarger, Jr. |
| 5,567,806 | A | 10/1996 | Abdul-Malak et al. |
| 5,571,216 | A | 11/1996 | Anderson |
| 5,580,923 | A | 12/1996 | Yeung et al. |
| 5,667,839 | A | 9/1997 | Berg |
| 5,677,839 | A | 10/1997 | Kondo et al. |
| 5,756,678 | A | 5/1998 | Shenoy et al. |
| 5,895,412 | A | 4/1999 | Tucker |
| 5,931,800 | A | 8/1999 | Rasmussen et al. |
| 5,997,895 | A | 12/1999 | Narotam et al. |
| 6,149,609 | A | 11/2000 | Lieberman et al. |
| 6,270,793 | B1 | 8/2001 | Van Dyke et al. |
| 6,274,155 | B1 | 8/2001 | Van Dyke et al. |
| 6,361,551 | B1 | 3/2002 | Torgerson et al. |
| 6,375,672 | B1 | 4/2002 | Aksan et al. |
| 6,454,787 | B1 | 9/2002 | Maddalo et al. |
| 6,461,628 | B1 | 10/2002 | Blanchard et al. |
| 6,500,464 | B2 | 12/2002 | Ceres et al. |
| 6,706,684 | B1 * | 3/2004 | Bayon et al. .................. 514/17.2 |
| 6,939,562 | B2 | 9/2005 | Spiro et al. |
| 7,121,999 | B2 | 10/2006 | Abraham et al. |
| 7,429,241 | B2 | 9/2008 | Sommerich |
| 2002/0103542 | A1 | 8/2002 | Bilbo |
| 2003/0014126 | A1 | 1/2003 | Patel et al. |
| 2003/0130747 | A1 | 7/2003 | Abraham et al. |
| 2003/0220334 | A1 | 11/2003 | Wender et al. |
| 2004/0028738 | A1 | 2/2004 | Huang et al. |
| 2005/0008660 | A1 | 1/2005 | Kipke et al. |
| 2005/0175659 | A1 | 8/2005 | Macomber et al. |
| 2005/0226856 | A1 | 10/2005 | Ahlfors |
| 2005/0283256 | A1 | 12/2005 | Sommerich et al. |
| 2006/0029633 | A1 | 2/2006 | Kaiser et al. |

FOREIGN PATENT DOCUMENTS

| | | | |
|---|---|---|---|
| EP | 0428541 A1 | 5/1991 | |
| EP | 0440198 | 8/1991 | |
| EP | 0667352 | 8/1995 | |
| EP | 0681431 A1 | 11/1995 | |
| EP | 0742018 | 11/1996 | |
| EP | 0877761 | 11/1998 | |
| EP | 0943346 | 9/1999 | |
| EP | 1084720 | 3/2001 | |
| EP | 1364627 | 11/2003 | |
| EP | 1484070 | 12/2004 | |
| EP | 1561480 A2 | 8/2005 | |
| EP | 1 738 70 A2 * | 1/2007 | |
| JP | 08041425 | 2/1996 | |
| WO | 9416570 A1 | 8/1994 | |
| WO | 9420133 | 9/1994 | |
| WO | 9617633 | 6/1996 | |
| WO | 9625961 | 8/1996 | |
| WO | 9638541 A1 | 12/1996 | |
| WO | 9640174 | 12/1996 | |
| WO | 9728192 | 8/1997 | |
| WO | 9728193 | 8/1997 | |
| WO | 9737694 | 10/1997 | |
| WO | 9913902 | 3/1999 | |
| WO | 9961518 A1 | 12/1999 | |
| WO | 0166162 A1 | 9/2001 | |
| WO | 2004078120 A2 | 9/2004 | |
| WO | 2006066327 | 6/2006 | |

OTHER PUBLICATIONS

Li, et al, The Development of Collagen Nerve Conduits that Promote Peripheral Nerve Regeneration, Biotechnology and Polymers (C. Gebelein ed.), 281-293 (1991).

Li, Shu-Tung, "Peripheral Nerve Repair with Collagen Conduits", Clin. Materials, 1992, 9:195-200.

MacFarlane, M. and Symon, L., Lyophilised dura mater: experimental implantation and extended clinical neurosurgical use, J. Neur. Neursurg. Psych., vol. 42, No. 9, pp. 854-858 (1979).

Madison et al.; "Factors Contributing to Preferential Motor Reinnervation in the Primate Peripheral Nervous System"; J. of Neuroscience, 1999, vol. 19 (24); 11007-11016.

Madison, R. et al, Point Sources of Schwann Cells Result in Growth into a Nerve Ebtubulation Repair Site in the Absence of Axons: Effects of Freeze-Thawing, Experimental Neurology, vol. 128, pp. 266-275 (1994).

Mamata et al, Microfibrillar collagen hemostat, JPN J. Neurosurg., vol. 3, No. 4, pp. 354-359 (1994).

McGregor, D. et al, Avitene Granulomas of Colonic Serosa, Ann. Clin. Lab. Sci., vol. 16, No. 4, pp. 296-302 (1986).

Meddings, N. et al, Collagen Vicryl—A New Dural Prosthesis, Acta Neurochirurgica, vol. 117, pp. 53-58 (1992).

Nakajima, M. et al, An Intraperitoneal Tumorour Mass caused by Granulomas of Microfibrillar Collagen Hemostat (Avitene), Arch Pathol Lab Med., vol. 119:1161-1163 (1995).

Narotam, P. et al., A Clinicopathological Study of Collagen Sponge as a Dural Graft in Neurosurgery, J. Neurosurg., vol. 82, pp. 406-412 (1995).

Narotam et al., Collagen Matrix (Duragen) in Dural Repair: Analysis of a New Modified Technique, SPINE, vol. 29, No. 24, pp. 2861-2867 (2004).

Narotam et al., Collagen Matrix (Duragen) in spinal durotomy: technique appraisal and clinical results, The Spine Journal, vol. 3, pp. 147S-148S (2003).

Narotam, P. et al., Experimental Evaluation of Collagen Sponge as a Dural Graft, British J. Neurosurg., vol. 7, pp. 635-641 (1993).

Narotam et al., Operative Sepsis in Neurosurgery: A method of Classifying Surgical Cases, Neurosurg., vol. 34, No. 3, pp. 409-416 (Mar. 1994).

Notification of the Safety Requirements for Drugs Produced of Body Components of Cattle, Sheep or Goats to Avoid the Risk of Transmission of BSE or Scrapie (Fed. Reg. No. 40, Feb. 26, 1994).

Nussbaum et al, Vicryl (polyglactin 910) mesh as a dural substitute in the presence of pia arachnoid injury, J. Neurosurg., vol. 71, No. 1, pp. 124-127 (Jul. 1989).

O'Neill, P., et al., Use of Porcine Dermis as a Dural Substitute in 72 Patients, J. Neurosurg., vol. 61, pp. 351-354 (1984).

Otani, I. et al, A Case of Intracranial Granuloma as a Complication of Microfibrillar Collagen Hemostat, J. for the St. Marianna Med. Sch., vol. 18, No. 6, pp. 994-999 (1990).

Rabinowitz et al. "Growth of rat cortical neurons on DuraGen, a collagen=based dural graft matrix" Neurological Reasearch, 2005, vol. 27, pp. 887-894 XP008081483.

Rohwer, R.G., "Analysis of Risk to Biomedical Products Developed from Animal Sources (with Special Emphases on the Spongiform Encephalopathy Agents, Scrapie and BSE)", National Library of Medicine Medline Database, TBIS, 2003, abstract, p. 5.

Public Health Issues Related to Animal and Human Spongiform Encephalopathies: Memorandum from a WHO Meeting, Bulletin of the World Health Org., vol. 70, Issue 2, pp. 183-190 (1992).

Safar, J. et al., "Thermal Stability and Conformational Transitions of Scrapie Amyloid (Prion) Protein Correlate with Infectivity", National Library of Medicine Medline Databse, TBIS, 2003, Abstract, p. 5.

Saltzman et al, Antibody diffusion in human cervical mucus, Biophysical Journal, vol. 66, No. 2, pp. 508-515 (1994).

San-Galli et al, Experimental Evaluation of a Collagen-coated Vicryl Mesh as a Dural Substitute, Neurosurg., vol. 30, No. 3, pp. 396-401 (1992).

Schmidt et al, Chain Dynamics, Mesh Size, and Diffusive Transport in Networks of Polymerized Actin: a quasielectric light scattering and microfluorescence study, Macromolecules, vol. 22, No. 9, 3638-3649 (1989).

Sickmueller, B., Rubmann, D., BSE and Scrapie—German Federal Health Office (BGA) on Safety Measures to be Adopted for Medicinal Products, Drugs Made in Germany, vol. 37, Issue 2, pp. 36-49 (1994).

Stein, M. et al., Collagen Sponge as a Topical Hemostatic Agent in Mucogingival Surgery, J. Periodontol, pp. 35-38 (Jan. 1985).

Tateishi et al., "Practical Methods for chemical Inactivation of Creutzfeldt-Jakob Disease Pathogen", National Library of Medicine Medline Database, TBIS, 2003, Abstract, p. 7.

Taylor, D.M., "Inactivation of SE Agents", National Library of Medicine Medline Database ITBIS, 2003, Abstract, p. 6.

Taylor, D.M., "Inactivation of BSE Agent", National Library of Medicine Medline Database, TBIS, 2003, Abstract, p. 7.
Taylor et al., "Unconventional Transmissible Agents in Dura Matter: Significance for Iatrogenic Creutzfeldt-Jakob Disease", Neuropathology & Applied Neurobiology, 1996, 22: 259-260.
Taylor, D.M., Inactivation of the Unconventional Agents of Scrapie, Bovine Spongiform Encephalopathy and Creutzfeldt-Jakob Disease, J. Hosp. Infection, vol. 18 (Supplement A), pp. 141-146 (1991).
Tarlov, I., Structure of the nerve root, Arch. Neuro. Psych., vol. 37, No. 3, pp. 555-583 (1937).
Thompson et al., "Hemorrhage Associated with Silastic Dural Substitute", J. of Neurology, Neurosurgery & Psychiatry, 1994, 57: 646-648.
Tsuruno, T., et al., An Arachnoid Plasty Technique Using a Collagen Seat and Fibrin Glue, Jpn. J. Neurosurg., vol. 4, No. 2, pp. 193-195 (1995) (with translation & certificate of translation).
Visser C., Voute A., Costing J., Boon M., Kok L.: Microwave irradiation and cross-linking of collagen, Biomaterials, 1992, vol. 13, No. 1, pp. 34-37, XP002443453.
Wada, T. et al, A Foreign-body Granuloma due to Microfibrillar Collagen Hemostat Used during a Craniotomy: A Case Report,, JPN J. Neurosurg., vol. 3, No. 5, pp. 442-445 (1994).
Wagner, W., Pachence, J., Ristich, J., Johnson, P., Comparative in Vitro Analysis of Topical Hemostatic Agents, J. Sur. Res., pp. 100-108 (1996).
Yamagata, S. et al, Clinical Experience with Expanded Polytetrafluoroethylene Sheet Used as an Artificial Dura Mater, Neuro Med Chir, vol. 33, pp. 582-585 (1993).
"Collagen Matrix, Inc., Launches DuraMatrixa Collagen Dura Substitute Membrane, Neuroflexa Flexible Collagen Nerve Cuff, and NeuroMatrixa Collagen Nerve Cuff" May 9, 2005, one page, XP002443455, Retrieved from the Internet: URL:http://www.collagenmatrix.com/PDF/05092005.pdf.
Abbott, W., and Dupree Jr., E., Clinical results of lyophilized human cadaver dura transplantation, J. Neurosurg., vol. 34, pp. 770-773 (Jun. 1971).
Adegbite et al., The role of neomembranes in formation of hematoma around Silastic dura substitute, J. Neurosurg., vol. 58, pp. 295-297 (Feb. 1983).
Amundson, G., Minimizing Blood Loss During Thoracolumbar Spine Surgery, Surgery For Spinal Cord Injuries 45-69 (S. Garfin & B. Northrup eds., 1993).
Anson et al, Bovine pericardium for dural grafts: clinical results in 35 patients, Neurosurgery, vol. 39, No. 4, pp. 764-768 (Oct. 1996).
Archibald et al., "A Collagen Based Nerve Guide Conduit for Peripheral Nerve Repair; An Electrophysiological Study of Nerve Regeneration in Rodents and Nonhuman Primates", J. of Comparative Neurology, 1991, 306: 685-696.
Archibald et al., "Long Term Maintenance of Axonal Regeneration in Primates Following Collagen Nerve Guide Repair of 2CMMedian Nerve Deficit", Society for Neuroscience Abstracts, 1992, vol. 18, Part1, Abstract.
Archibald et al., "Monkey Median Nerve Repaired by Nerve Graft or Collagen Nerve Guide Tube", J. of Neuroscience, 1995, 15(5): 4109-4123.
Archibald et al, Semi-Permeable Collagen Based Nerve Guide Tubes are as Effective as Standard Nerve Grafts to Repair Transected Peripheral Nerves: An Electrophysiological Study in the Non-Human Primate, Soc. Neuro. Abs., vol. 15, p. 318 (1989).
Avery, N. and Bailey, A., An Efficient Method for the Isolation of Intramuscular Collagen, Meat Science, vol. 41, No. 1, pp. 97-100 (1995).
Brown et al., "A Simple and Effective Method for Inactivating Virus Infectivity in Formalin-fixed Tissue Samples from Patients with Creutzfeldt-Jakob Disease", National Library of Medicine Medline Database, TBIS, 2003, Abstract, p. 8.
Brown et al., "Effect of Chemicals, Heat and Histopathologic Processing on High-Infectivity Hamster-Adapted Scrapie Virus", National Library of Medicine Medline Database, TBIS, 2003, Abstract, p. 10.
Brown et al.,"Newer Data on the Inactivation of Scrapie Virus or Creutzfeldt-Jakob Disease Virus in Brain Tissue", J. Infectious Dis., vol. 153, No. 6, pp. 1145-1148 (Jun. 1986).

BSE Transmission and Medicines, Reg. Affairs J., pp. 207-209 (Mar. 1992).
Campbell et al., Clinical use of freeze-dried human dura matter. J. Neurosurg., vol. 15, No. 2, pp. 208-214 (1958).
Cantore et al., Neurosurgical use of human dura matter sterilized by gamma rays and stored in alcohol: long-term results, J. Neurosurg. vol. 66, pp. 93-95 (Jan. 1987).
Chvapil, M., Collagen sponge: Theory and practice of medical applications, J. Biomed. Mater. Res., vol. 11, pp. 721-741 (1977).
Cho, H. J., "Inactivation of the Scrapie Agent by Pronase", National Library of Medicine Medline Database, TBIS, 2003, Abstract, p. 10.
Collins et al., "Use of Collagen Film as Dural Substitute: Preliminary Animal Studies", J. of Biomedical Material Research, 1991, 25:267-276.
Commission of the European Communities, Ad Hoc Working Party on Biotechnology/Pharmacy, Note for Guidance: Guidelines for Minimizing the Risk of Transmission of Agents Causing Spongiform Enecphalopathies via Medicinal Products, Draft No. 2 (May 1991).
Cox., "A Systematic Review of the Published Literature to Identify the Methods of Inactivation for Unconventional Agents of Transmissible Spongiform Encephalopathies", Medical Devices Agency, UK, 2001, pp. 1-13.
Dagalakis et al., Design of an artificial skin. Part III. Control of pore structure, J. Biomed. Matls. Res., vol. 14, 511-528 (1980).
Dees et al., "Inactivation of the Scrapie Agent by Ultraviolet Irradiation in the Presence of Chlorpromazine", National Library of Medicine Medline Database, TBIS, 2003, Abstract, p. 9.
DiMartino et al., "Inactivation of the Scrapie Agent in a Scaled-down Procedure for the Purification of Gangliosides from Brain Tissue", National Library of Medicine Medline Database, TBIS, 2003, Abstract, p. 7.
Doillon et al., "Chemical Inactivators as Sterilization Agents for Bovine Collagen Materials", National library of Medicine Medline Database, TBIS, 2003, Abstract, p. 3.
Doillon, C.J. et al., Collagen-Based Wound Dressings: Control of the Pore Structure and Morphology, J. Biomed. Matls. Res., vol. 20, 1219-1228 (1986).
Doillon, C.J. et al., Collagen-Based Wound Dressing: Effects of Hyaluronic Acid and Fibronectin on Wound Healing, Biomaterials, vol. 7, pp. 3-8 (1986).
Doillon et al., Fibroblast & Epidermal Cell-Type I Collagen Interactions: Cell Culture and Human Studies, Scanning Microscopy, vol. 2, No. 2, pp. 985-992 (1988).
Doillon et al., Fibroblast-Collagen Sponge Interactions and the Spatial Deposition of Newly Synthesized Collagen Fibers In Vitro and In Vivo, Scannin Electron Microscopy, Part 3 , pp. 1313-1320 (1984).
Doillon et al., "Transmission of Creutzfeldt-Jakob Disease by Handling of Dura Matter", The Lancet, 1993, 341: 123-124.
Dormont, D., "How to Limit the Spread of Creutzfeldt-Jakob Disease", National Library of Medicine Medline Database, TBIS, 2003, Abstract, p. 4.
Dubuisson & Kline, "Indications for peripheral nerve & brachial plexus surgery," Neurology of Trauma, vol. 10, No. 4, pp. 935-951 (1992).
Dufrane D., Cornu O., Schneider, Y.J.: "Physical and chemical procesing for a human dura mater substitute" Biomaterialsvol. 23, 2002, pp. 2979-2988, XP002443454.
Eismont et al., Treatment of dural tears associated with spinal surgery, J. Bone Joint Surg., vol. 63-A, No. 7, pp. 1132-1136 (1981).
Ernst & Race, "Comparative Analysis of Scrapie Agent Inactivation Methods", National Library of Medicine Medline Database, TBIS, 2003, Abstract, p. 6.
Goldstein et al, Development of a reconstituted collagen tendon prosthesis, J. Bone Joint Surg., vol. 71-A, No. 8, pp. 1183-1191 (1989).
Gondo, G. et al, Peculiar computed tomographic images after intracrania use of microfibrillar collagen hemostat: report of three cases, Neurol. Surg., vol. 17, No. 11, pp. 1067-1071 (1989).
Hoffman et al., Septo-hippocampal regeneration through biosynthetic bridges containing adult Schwann cells, Soc. Neuro. Abs., vol. 18, Pt. 1, 271.1 (1992).
Ishkawa, H. et al, Rinsho to Kenkyu, Clinical Study and Investigation, vol. 61, No. 4, pp. 1315-1321 (1984).

Janetta et al., "Formaldehyde-Treated Regenerated Collagen Film and Film-Laminate as a Substitute for Dura Mater", Proceedings of the 21st Annual Sessions of the Forum on Fundamental Surgical Problems, 51st Clinical Congress of the American College of Surgeons, Atlantic City, New Jersey, 1965, Surgical Forum, vol. XVI, pp. 435-437.

Jenq et al, Nerve Regeneration Changes with Filters of Different Pore Size, Experimental Neurology, vol. 97, pp. 662-671 (1987).

Keller et al., Repair of spinal dural defects with vicryl (polyglactin 910) mesh. J. Spinal Disorders, vol. 2, No. 2, pp. 87-92 (1989).

Kelly et al., Collagen Sponge Repair of Small Cerebrospinal Fluid Leaks Obviates Tissue Grafts and Cerebrospinal Fluid Diversion after Pituitary Surgery, Neurosurg., vol. 49, No. 4, pp. 885-890 (Oct. 2001).

Kline, "Dural Replacement with Resorbable Collagen", Arch Surg, 1965 91: 924-929.

Kline, D. and Hayes, G., The use of a resorbable wrapper for peripheral-nerve repair. J. Neurosurg., vol. 21, No. 9, pp. 737-750 (Sep. 1964).

Krarup et al., "Factors that Influence Peripheral Nerve Regeneration: An Electrophysiological Study of the Monkey Median Nerve", Annals of Neurology, 2002, 51: 69-81.

Kuntz, R. and Saltzman, W., Neutrophil Motility in Extracellular Matrix Gels-: Mesh Size and Adhesion Affect Speed of Migration, Biophysical Journal, vol. 72, No. 3, pp. 1472-1480 (Mar. 1997).

Kurze et al., Collagen sponge for surface brain protection. J. Neurosurg., vol. 43, No. 5, pp. 637-638 (1975).

Laquierre et al., Experimental evaluation of bilayered human collagen as a dural substitute, J. Neurosurg., vol. 78, pp. 487-491 (Mar. 1993).

Laun et al., Comparative study of lyophilized human dura mater and lyophilized bovine pericardium as dural substitutes in neurosurgery, Acta. Neurochirurgica, vol. 107: 16-21 (1990).

Li et al, Semipermeable Collagen Nerve Conduits for Peripheral Nerve Regeneration, Polymeric Materials Science and Engineering, vol. 62, pp. 575-583 (1990).

Notification on the Marketing Authorisation and registration of drugs, Measures to avert risks associated with drugs, stage II (German Federal Institute for Drugs and medical Products, Mar. 28, 1996).

* cited by examiner

FLOWABLE COLLAGEN MATERIAL FOR DURAL CLOSURE

FIELD

The present application relates to flowable collagen dural graft materials for repairing, replacing, reinforcing or strengthening bodily tissue, as an adhesion barrier, or for use as a short-term body contact for moisture retention, hemostasis or tissue protection.

BACKGROUND

The human brain and spinal cord are protected, preserved and enveloped by a meningeal system comprising meningeal membranes. A meningeal membrane is composed of an intricate network of three overlapping tissue layers: the dura mater (or dura) outermost layer, the arachnoid middle layer, and the pia mater innermost layer. The outermost layer is tough and waterproof. The innermost layer follows along and contacts the entire surface of the brain and spinal cord, carrying blood vessels to service them. The middle layer acts as a gliding system between the inner and outer surfaces. Any damage to this network causes acute problems to the central nervous system.

Repairing damaged meningeal membranes has largely focused on implantable and/or resorbable constructs known as dural substitutes. These dural substitutes are grafted to the damaged dura mater and are designed to replace and/or regenerate the damaged tissue. A number of synthetic and animal based dural repair products are currently available. However, most of these are categorized into either suturable or onlay (sutureless) grafts, typically available in sponges, sheets, nonwoven matrixes or combinations thereof. In some instances, these products can be difficult to apply, and in some cases limited pliability, or moldability, may not enable them to adequately reach the entire damaged area.

Synthetic gelatin and polymeric dural sealants have also been disclosed. However, with these synthetic sealants, certain problems persist as well. Some are porous, therefore not creating a tight seal. They may also be nonelastic and/or insoluble, thus leading to time consuming application. Furthermore, most are subject to swelling once applied and/or implanted because they must be hydrated or mixed at the surgical site rather than being prepared in advance of the procedure. Swelling of the material, post implantation, can be detrimental to the patient, for example, where such swelling causes compression of brain tissue, a nerve root or the spinal cord.

Thus, there is a need for a dural graft material that is especially adapted for use in those areas or locations where it is difficult to apply conventional dural grafts. Furthermore, there is a need for a dural graft material which minimizes or eliminates post implantation swelling as well as reduces the quantity of implant material necessary to repair the damage. Finally, a dural graft material is needed which simplifies the procedure in terms of mateability, risks and time duration as compared with conventional dural graft products.

SUMMARY

The present invention provides a flowable collagen graft materials useful, for example, as a dural graft. These graft materials comprise a collagen powder and a liquid in an amount effective to impart a flowable consistency for application to an area of concern. The collagen graft materials, when used as a dural graft, are sufficiently flowable so as to provide both superior contact with and easier access to a surgical site than typical, more rigid dural grafts such as collagen sheets or synthetic gelatin or polymeric dural sealants. The flowable graft materials are moldable and/or extrudable and have particular application in areas where other materials simply cannot access a site because they lack adequate pliability or moldability.

The flowable collagen graft materials can also be used in applications to reduce and/or eliminate post implantation problems associated with other materials (synthetic dural sealants (hemostasis products)), such as product swelling after application and implantation.

In another aspect, there is provided a method for repairing damaged dura utilizing the flowable collagen graft materials described herein. In one aspect the method involves applying a flowable dural graft material comprising a mixture of collagen and a liquid to a desired site, and conforming the dural graft material to a curvature of the site. The flowable graft material can be applied through a variety of techniques, including by ejections from a syringe and by manual spreading.

DETAILED DESCRIPTION

Certain exemplary embodiments will now be described to provide an overall understanding of the principles of the structure, function, manufacture, and use of the devices and methods disclosed herein. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

One aspect of the invention provides a dural graft material that can be dispensed in a flowable, fluidized, gel-like and/or paste-like form and, during application, shaped to conform to and remain in place in a desired location. In use as a dural substitute or adhesion barrier, or for short-term body contact for moisture retention, hemostasis, or tissue protection, the flowable dural graft material may be placed in contact with the desired bodily tissue. Once implanted at the desired site, contact between the flowable collagen material and the bodily tissues is maintained as a result of the paste-like consistency of the material. Over time, usually about 3 to 6 months, the flowable collagen material will be fully resorbed.

A flowable collagen material in accordance with the present application can be formed from a collagen powder and a liquid in an amount effective to impart a flowable consistency to the resulting product. This flowable product, which is gel-like and/or paste-like in consistency, can be applied to the desired location by a number of techniques, as described below. Further, as a result of being a flowable material, the dural graft material described herein can be molded such that it is able to substantially conform to the geometery of the anatomical site at which it is implanted, e.g., the curvature of the site of dura damage.

The collagen source for the flowable dural substitute described herein can be obtained from a variety of sources as known to those skilled in the art. By way of example, such collagen sources may include, bovine collagen, such as Type 1 bovine collagen, as well as porcine collagen, porcine small intestine submucosa, and fetal bovine skin.

Generally, the collagen material is in a powdered form, however the powder can be derived from sheets of a collagen material that are ground to a powder having the desired particle size distribution. Exemplary collagen materials can be crosslinked, either before or after grinding the collagen to a powder form, but before combining with a liquid to form a flowable material. Alternatively, the flowable collagen graft material may be crosslinked by a variety of known techniques, including vapor crosslinking or solution crosslinking. Exemplary crosslinking agents include formaldehyde, glutaraldehyde, carbodiimides, and difunctional succinimides. The flowable collagen graft material may also be crosslinked by dehydrothermal crosslinking or UV radiation.

The particle size of the collagen material can vary depending on factors such as the desired use of the material as well as the properties desired of the flowable material. In one embodiment, the particle size of the collagen powder of the flowable dural graft material is in the range of about 0.1 to 10,000 microns. In another embodiment, collagen powder has a particle size in the range of about 10 to 1,000 microns. In yet another embodiment, the collagen powder has a particle size in the range of about 50 to 800 microns. In further embodiment, collagen powder has a particle size in the range of about 100 to 400 microns.

One skilled in the art will appreciate that a variety of biocompatible liquids can be mixed with the collagen material to form the flowable graft material. Exemplary liquids include water (e.g., purified water), saline, blood, plasma, collagen gels, and any other biocompatible solvents commonly used in the art.

The relative amounts of collagen and liquid used to form the flowable dural graft material can vary depending on the desired applications and properties. One skilled in the art can readily determine the appropriate ratios of these components to achieve a flowable graft material that is suitable for a desired use and application technique. For example, flowable materials that are to be injectable, such as through a conventional syringe, should generally be less viscous than a flowable dural graft material that is to be applied by other techniques, such as by manual application. One skilled in the art will appreciate that conventional syringes have a standard luer lock at the distal end. However, a custom syringe with a different size opening can be designed to allow a thicker, more viscous material to be delivered. Consistent with these qualifications, the collagen powder component can generally be present in an amount of about 25% wt/wt %. In another embodiment, the collagen powder component can be present in an amount of about 20% wt/wt %. In a further embodiment, the collagen powder component can be present in an amount of about 11% wt/wt %. In yet another embodiment, the collagen powder component can be present in an amount of about 6% wt/wt %.

One skilled in the art will appreciate that a variety of additives can be incorporated into the flowable graft material. Examples of such additives include, in effective amounts, antimicrobial agents, bioactive compounds, growth factors, immunosuppressive agents, permeation enhancers, antiviral agents, antitumor agents, and gelling agents. The flowable graft material may also include effective amounts of meningeal tissue growth factors.

The flowable graft material described herein can be used as dural graft, or it can be used in a variety of other applications, including as an adhesion barrier, for short-term body contact for moisture retention, hemostasis, and tissue protection. Although the flowable graft and its method of use is primarily described in the context of a dural graft, one skilled in the art will understand the additional uses and applications of such a material. Independent of the intended use, the flowable collagen material can be deliverable in a fluidized, paste or gel state. One exemplary method for applying the material is by ejection from a delivery device such as a syringe. The material can be applied by ejection from a delivery device in the desired pattern or it can be applied by other techniques (e.g., manually or by other handling tools) and subsequently shaped to the desired pattern. For example, for thicker pastes, the material may be ejected with a caulking gun or similar type system In one embodiment, the dural graft material is prepared before it is applied to a surgical site. However, the material may also be prepared simultaneously with application to the surgical site.

One use of the flowable collagen graft is in a surgical procedure as a dural graft material to repair or protect damaged meningeal membranes. The graft material can be implanted by applying an effective amount of the flowable collagen graft by the desired application technique (e.g., by ejection from a delivery device) through an opening of the cranium and is placed in contact with the meningeal membrane at the area of concern. An effective amount of the flowable collagen dural graft material may comprise a volume sufficient to slightly overlap with and contact a portion of non-damaged meningeal membrane. The flowable nature of the graft material enables it to substantially conform to the curvature of the meningeal membrane. In addition, the flowable graft material provides a superior seal and advantageously effectively avoids gaps between the graft material and the meningeal membrane. Further advantages of this material as a dural graft include its fluid impermeable nature and its ability to be implanted in a sutureless manner.

EXAMPLE

A non-limiting example illustrating the preparation of a flowable dural graft material in accordance with the present invention is provided below. Bovine collagen (Type I Tendon sheet) is ground into powder having an average particle size of 100-500 microns. The collagen powder is then added to saline in the following four ratios to determine the weight percent lower limit for applying the material to the site of dural damage in a conventional 60 ml syringe:

(A) 25% wt/wt % collagen powder (0.511 g bovine collagen powder to 2.0 ml saline);
(B) 20% wt/wt % collagen powder (0.511 g bovine collagen powder to 2.5 ml saline);
(C) 11% wt/wt % collagen powder (0.511 g bovine collagen powder to 4.5 ml saline);
(D) 6% wt/wt % collagen powder (0.511 g bovine collagen powder to 8.5 ml saline). The product resulting from sample (A) is a thick paste that is too thick to be suitable for ejection from a conventional 60 ml syringe and it is not moldable. The product resulting from sample (B) is a balled thick paste that is moldable and it likewise is not ejectable from a conventional 60 ml syringe. However, this material may be applied to the site of dura damage by other application techniques such as using a custom syringe with a larger opening, delivering the material as a log shape and then spreading over the defect, or using a delivery system with mechanical advantage such as a caulking gun. The product resulting from sample (C) is not tacky, resists "wash away" when some additional saline is added to the material, and is both moldable and ejectable from a conventional 60 ml syringe. The product resulting from sample (D) is also moldable and ejectable from a conventional 60 ml syringe.

One skilled in the art will appreciate further features and advantages based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A method for repairing a damaged dura comprising:
    applying a flowable dural graft material comprising a mixture of cross-linked collagen and a liquid to a desired site of dural damage, wherein said collagen is cross-linked prior to the addition of said liquid; and conforming the dural graft material to a curvature of the site of dural damage.

2. The method of claim 1, wherein the collagen is present in an amount of about 6% wt/wt %.

3. The method of claim 1, wherein the collagen source is a collagen powder having a particle size in the range of about 10 to 1000 microns.

4. The method of claim 1, wherein the flowable graft material is applied by ejection from a syringe.

5. The method of claim 1, wherein the flowable graft material is applied manually.

* * * * *